(12) United States Patent
Hsieh et al.

(10) Patent No.: US 7,258,441 B2
(45) Date of Patent: Aug. 21, 2007

(54) EYE ACTIVITY MONITORING APPARATUS AND SYSTEM

(76) Inventors: Chi Wen Hsieh, No. 3, Lane 5, Cihguang St., Dasi Township, Taoyuan County 355 (TW); Tai Lee Chen, 2F., No. 60, Lane 1, Ronghua 3rd., Beitou District, Taipei City 112 (TW); Tai Lang Jong, No. 100-8, Jianjhong Rd., Hsinchu City 300 (TW)

( * ) Notice: Subject to any disclaimer, the term of this patent is extended or adjusted under 35 U.S.C. 154(b) by 544 days.

(21) Appl. No.: 10/866,924

(22) Filed: Jun. 14, 2004

(65) Prior Publication Data

US 2005/0179865 A1 Aug. 18, 2005

(51) Int. Cl.
*A61B 3/14* (2006.01)
*G08B 23/00* (2006.01)

(52) U.S. Cl. ....................... 351/206; 340/575
(58) Field of Classification Search ........ 351/200–209; 340/575, 576
See application file for complete search history.

(56) References Cited

U.S. PATENT DOCUMENTS 5,570,698 A * 11/1996 Liang et al. ................. 600/558
5,786,765 A * 7/1998 Kumakura et al. .......... 340/576
6,003,991 A * 12/1999 Viirre ........................ 351/206
6,097,295 A * 8/2000 Griesinger et al. .......... 340/576

* cited by examiner

*Primary Examiner*—Ricky Mack
*Assistant Examiner*—M. Hasan
(74) *Attorney, Agent, or Firm*—Egbert Law Offices

(57) ABSTRACT

The present eye activity monitoring system includes a monitoring apparatus for acquiring the eye image of a user in a closed eye state and an image-processing apparatus for generating an alarm signal based on the eye image. The monitoring apparatus includes an eye mask, an image-sensing unit positioned on the eye mask, a control circuit electrically connected to the image-sensing unit, a transmitting module electrically connected to the control circuit, an antenna electrically connected to the transmitting module and at least on power supply positioned on the eye mask. The image-processing apparatus has a receiving module and an image-processing module. The image-processing module judges the eye status according to the acquired feature of the eye image, and sends a warning alarm to trigger the warning device when an abnormal event occurs.

18 Claims, 3 Drawing Sheets

EYE ACTIVITY MONITORING APPARATUS AND SYSTEM

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to an eye activity monitoring apparatus and system, and more particularly, to an eye activity monitoring apparatus and system for a user during sleep.

BACKGROUND OF THE INVENTION

Since the development of the medical science and the living condition result in longer and longer human lifespan, the aged society is impending. However, aged people often suffer from diseases such as cardiovascular disease and diabetes, which are serious threats endangering the life quality of the aged people, since these diseases are apt to break out suddenly. Therefore, researchers recently have utilized considerable resources on developing medical equipment which functions such as family attendance for sending a warning alarm when a family member's disease suddenly breaks out. It is difficult to warn in advance when the aged person is asleep and a disease breaks out suddenly, and the aged person may die suddenly as a consequence if the family is careless or not present at such particular time. Although there are some medical equipment at the present that can be put on the aged people to send a message to medical organizations for emergency treatment by the monitoring of physiology signals, it is apparent such methods are departing from human nature and will harm the self-respect of the aged people.

At present, many physiology signal-sensing methods are invasive, contact type or activated through the patients to trigger the emergency treatment notification. However, such type of equipment has many problems such as resulting in discomforting the patients. In addition, it is possible that the patients tear apart the sensing components because of extreme pain or other factors generated from the breaking out of illness, which causes the sensing equipment to fail. Therefore, the current society is in great need of a type of monitoring equipment that will not cause discomfort to the patients but can send out physiology signals effectively, and especially can send alarm signal on time when the monitored person suffers from a certain abnormal situation during sleep.

BRIEF SUMMARY OF THE INVENTION

The objective of the present invention is to provide an eye activity monitoring apparatus and system for a user during sleep.

In order to achieve the above-mentioned objective, and avoid the problems of the prior art, the present eye activity monitoring system comprises a monitoring apparatus for acquiring the eye image of a user with the eye closed and an image-processing apparatus for generating an alarm signal based on the eye image analysis. The monitoring apparatus comprises an eye mask, an image-sensing unit positioned on the eye mask, a control circuit electrically connected to the image-sensing unit, a transmitting module electrically connected to the control circuit, an antenna electrically connected to the transmitting module and at lease one power supply positioned on the eye mask.

The image-processing apparatus comprises a receiving module and an image-processing module. The image-processing module comprises a noise reduction and image alignment unit, an image enhancement unit, a feature extraction unit, a judgment unit and a statistic unit. The noise reduction and image alignment unit depresses the noise upon receiving the eye image from the receiving module, and selects the mean position of the eyelash as a reference point to capture a frame with 64×64 pixels centered at the reference point for the subsequent analysis. The image enhancement unit enhances the eye image by the DoG (Difference of Gaussian) filter technology, and the feature extraction unit then acquires the feature of the eye image by the DWT (Discrete Wavelet Transform) technology. The judgment unit judges eye statuses according to the acquired feature of the eye image, and the statistic unit counts the historical records of the eye status and sends a warning alarm to trigger the warning device when an abnormal event occurs.

BRIEF DESCRIPTION OF THE SEVERAL VIEWS OF THE DRAWINGS

Other objectives and advantages of the present invention will become apparent upon reading the following description and upon reference to the accompanying drawings.

DETAILED DESCRIPTION OF THE INVENTION

Figure 1:
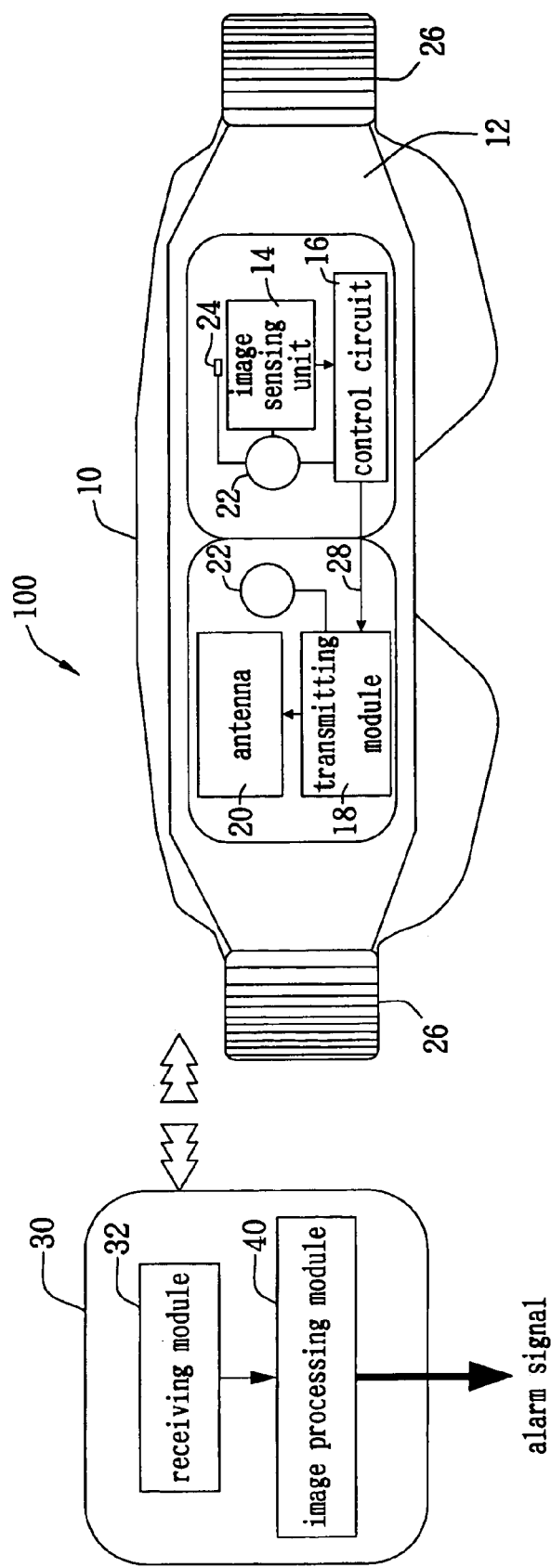
FIG. 1 illustrates perspective view of an eye activity monitoring system according to the present invention.

FIG. 1 illustrates an eye activity monitoring system 100 according to the present invention. The present invention adopts a design using the eye mask to meet the attendance requirements for the aged people. Especially, the present invention uses the large space of the eye mask to allocate the sensing components and RF (Radio Frequency) components. As shown in FIG. 1, the eye activity monitoring system 100 comprises a monitoring apparatus 10 for acquiring an eye image of a user in a closed-eye state and an image-processing apparatus 30 for generating an alarm signal based on the eye image analysis. The monitoring apparatus 10 comprises an eye mask 12, an image-sensing unit 14 positioned on the eye mask 12, a control circuit 16 electrically connected to the image-sensing unit 14, a transmitting module 18 electrically connected to the control circuit 16, an antenna 20 electrically connected to the transmitting module 18 and two power supplies 22 positioned on the eye mask 12. The transmitting module 18 is electrically connected to the control circuit 16 by a flexible printed circuit 28. The image-processing apparatus 30 comprises a receiving module 32 and an image-processing module 40.

Figure 2:
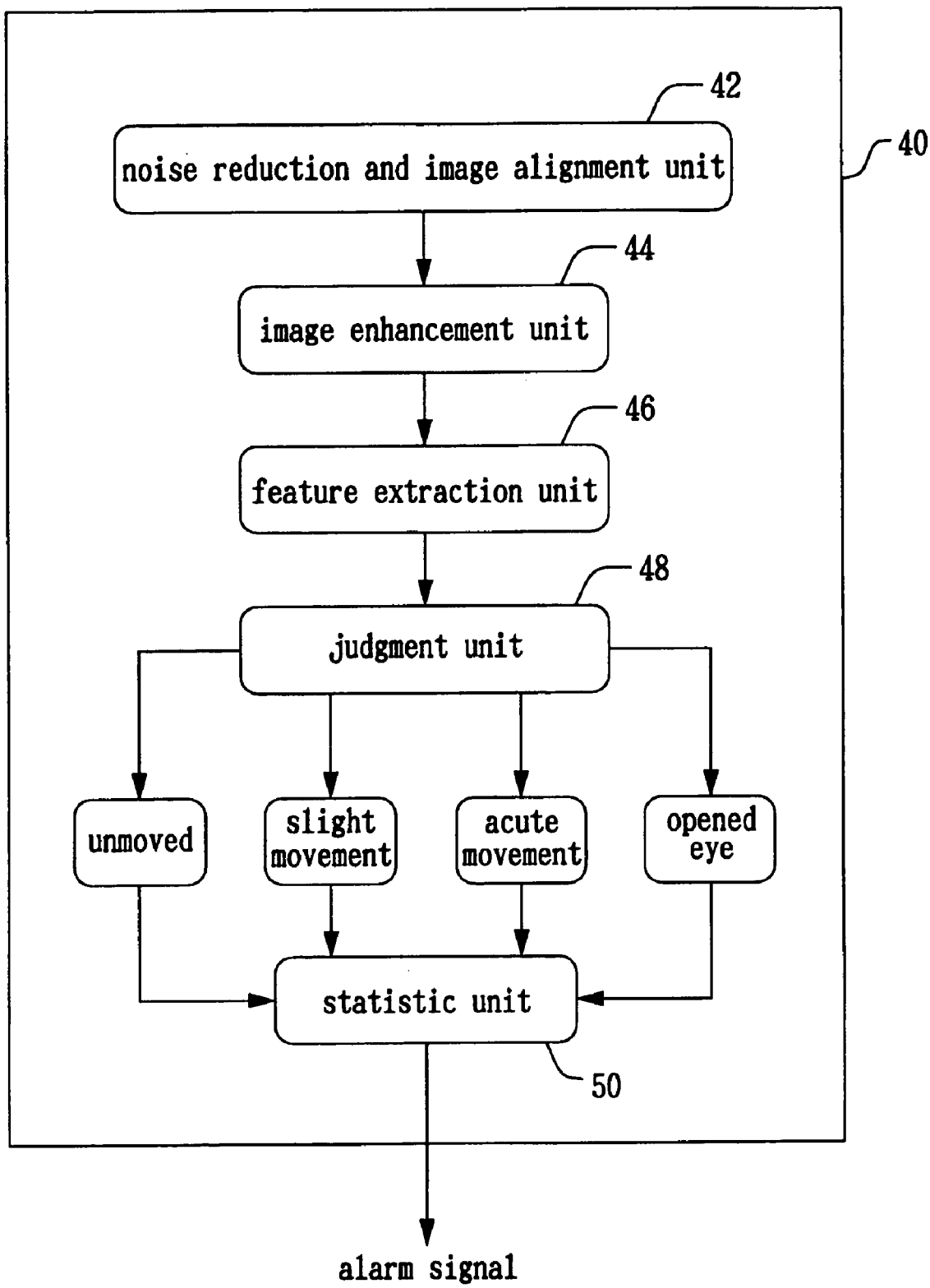
FIG. 2 shows a functional block diagram of the image-processing module according to the present invention.

FIG. 2 shows a functional block diagram of the image-processing module 40 according to the present invention. As shown in FIG. 2, the image-processing module 40 comprises a noise reduction and image alignment unit 42, an image enhancement unit 44, a feature extraction unit 46, a judgment unit 48 and a statistic unit 50. The eye image transmitted to the noise reduction and image location unit 42 consists of the eye image itself and the noise, wherein the noise source comprises the noise from the image-sensing unit 14, the channel noise and interference noise from the radio transmission. The noise reduction and image alignment unit 42 depresses the noise upon receiving the eye image from the receiving module 32. There may be a certain difference between positions of the user's face wearing the monitoring apparatus 10, therefore the present invention selects a reference point acting as the location point for the system analysis to eliminate the difference. Preferably, the present invention selects the mean position of the eyelash as the location to capture a frame with 64×64 pixels centered at the location for subsequent analysis.

The image enhancement unit 44 enhances the eye image by the DoG (Difference of Gaussian) filter technology, and the feature extraction unit 46 then acquires the feature of the eye image by the DWT (Discrete Wavelet Transform) technology. The judgment unit 48 judges eye statuses according to the acquired feature of the eye image, and categorizes these eye images into four statuses, i.e., eye-closed unmoved, eye-closed slight movement, eye-closed acute movement and eye-opened. The statistic unit 50 counts the historical records of the eye status, and sends a warning alarm to trigger the warning device when an abnormal event occurs (for example, no movements for a long time or no movement with eye opened).

Figure 3:
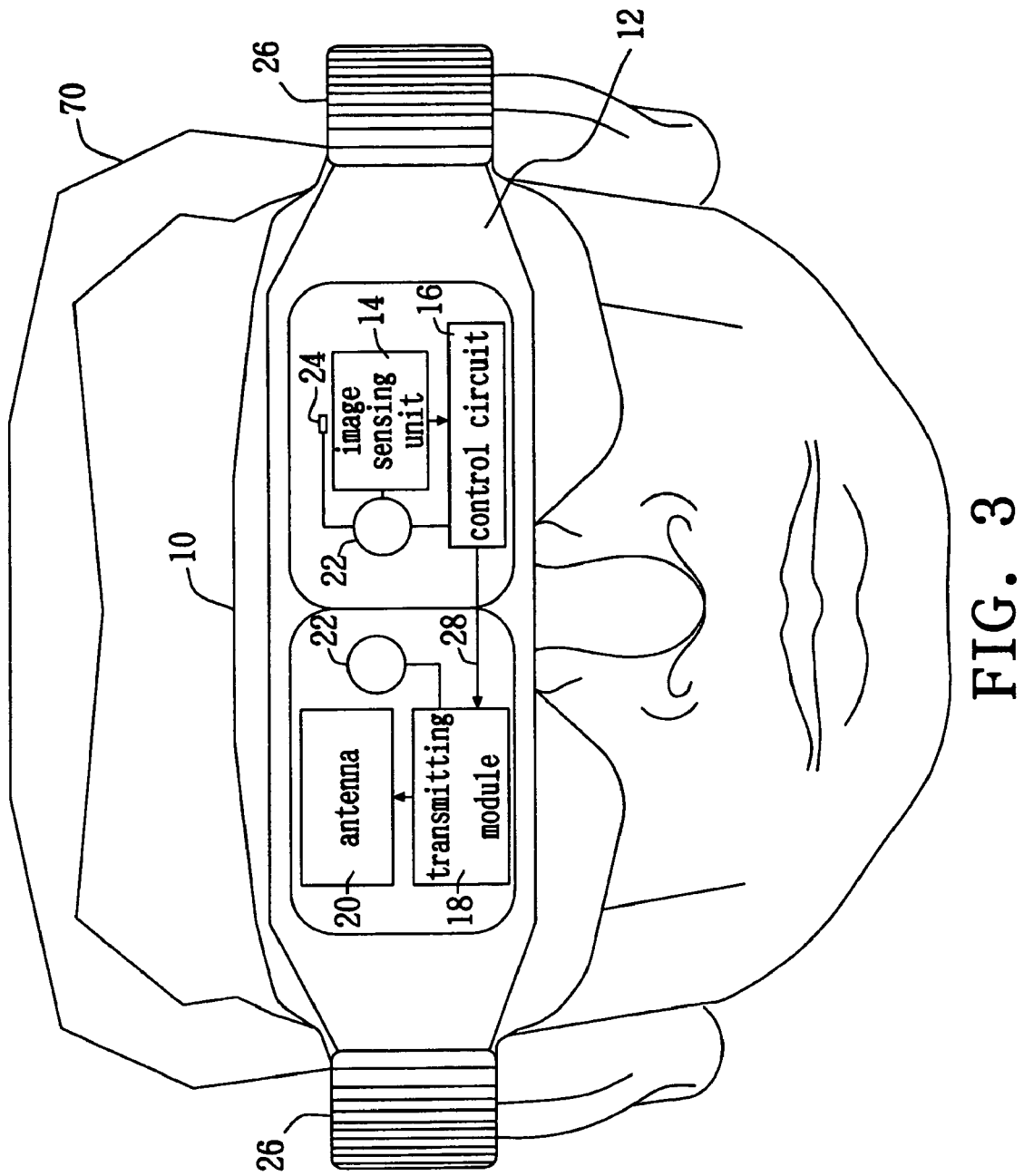
FIG. 3 shows a perspective view of an illustrative diagram of a user wearing the monitoring apparatus according to the present invention.

FIG. 3 shows an illustrative diagram of a user 70 wearing the monitoring apparatus 10 according to the present invention. The monitoring apparatus 10 is fixed at the head of the user 70 by an elastic band 26. The eye activity monitoring system 100 of the present invention can be used to monitor the eye activity when the user 70 lies down during sleep, and judge based on the captured image whether the abnormal event occurs to output the alarm signal. Under normal sleep, the human eye should be closed and the eyeballs will move irregularly. On the contrary, if heart attack or unexpected shock conditions occurs, the eyes status the user 70 will change. For example, under the shock status, his eyes will probably open and its pupil will enlarge with no movement. Therefore, the present invention can be used to monitor the physiological status of the user 70 and output an alarm signal to inform relative personnel to carry out emergency treatment when the abnormal event occurs.

The eye activity monitoring apparatus 10 can further comprise an LED (light-emitting diode) 24 positioned on the eye mask 12 for illuminating the eye of the user 70. In order to avoid disturbing the sleep of the user 70, the LED 24 can illuminate the human eyes with a low luminance of less than 0.3 lux. The image-sensing unit 14 can be a CCD (Charge Coupled Device) or CMOS (Complementary Metal-Oxide-Semiconductor Transistor), and is a sensor without infrared ray filter to ensure that the acquired images comprise the visible light and near infrared ray waveband. Furthermore, if the image-sensing unit 14 is a CCD or CMOS available on the current market, the focusing lens can be removed to further decrease the entire thickness of the image-sensing unit 14. However, it is unavoidable that the human privacy will be affected when the human body status is monitored by the image processing technique. Fortunately, the present invention removes the focusing lens and infrared ray filter, and therefore the acquired image is unrecognizable by the human eye's vision and the above-described suspicion can be avoided.

Assume the acquired frame of the image-sensing unit 14 has a 160×120 resolution with monochromic 8 bits output (i.e., each frame has 153600 bits) and the sampling frequency is one frame/second, the data rate of the eye image will be 153600 bits/sec. Furthermore, comparing the data rate of the captured eye image and the required overall data rate with the transmission protocol processing, the transmitting module 18 preferably has 1 Mbits/sec processing capability. In addition, since the present invention only transmits data between the monitoring apparatus 10 and the image-processing apparatus 30, the transmitting module 18 can use the ISM (Industrial, Scientific, and Medical) 2.4~2.5 GHz frequency which does not require a license. Additionally, in order to prevent signal interference and avoid the transmission interferences with other wireless equipments, the transmitting module 18 may use a GFSK (Gaussian Frequency Shift Keying), different from spread frequency technology used by the wireless network and Bluetooth, to modulate the eye image before transmitting to the image-processing device 30 by the antenna 20. The transmitting module 18 can optionally use the IEEE 802.11 or Bluetooth wireless transmission protocol to transmit the eye image to the image-processing apparatus 30.

The antenna 20 is preferably a planar antenna, which has an omni-directional radiation field in the horizontal plane when the user 70 lies down. Planar Inverted-F Antenna (PIFA) has the omni-directional radiation field in the horizontal plane, and can be a suitable candidate for the antenna 20 of the present invention. Since the planar antenna has the omni-directional radiation field in the horizontal plane, the receiving module 32 of the image-processing apparatus 30 can receive signal at any position around the antenna 20, while it has very weak radiation intensity in the eyeball direction to reduce the physiological influences on the head of the user 70. Furthermore, because the planar antenna has no protruding structure, it is quite suitable to be allocated on the eye mask without collisions with other components when the user 70 wears it.

The above-described embodiments of the present invention are intended to be illustrative only. Numerous alternative embodiments may be devised by those skilled in the art without departing from the scope of the following claims.

We claim:

1. An eye activity monitoring apparatus comprising:
   an eye mask;
   an image-sensing unit positioned on said eye mask;
   a control circuit electrically connected to said image-sensing unit;
   a transmitting module electrically connected to said control circuit; and
   an antenna electrically connected to said transmitting module.

2. The eye activity monitoring apparatus of claim 1, further comprising:
   at least one power supply positioned on said eye mask.

3. The eye activity monitoring apparatus of claim 1, further comprising:
   a light emitting diode positioned on said eye mask.

4. The eye activity monitoring apparatus of claim 1, wherein said image-sensing unit is a CCD or a CMOS image sensor.

5. The eye activity monitoring apparatus of claim 1, wherein said image-sensing unit is a sensor without an infrared ray filter and focus lens.

6. The eye activity monitoring apparatus of claim 1, wherein said antenna is a planar antenna.

7. An eye activity monitoring system comprising:
   a monitoring means for acquiring an eye image from a user in a closed-eye state; and
   an image-processing means for generating an alarm signal based on said eye image, said monitoring apparatus comprises:
      an eye mask;
      an image-sensing unit positioned on said eye mask;
      a control circuit electrically connected to said image-sensing unit;
      a transmitting module electrically connected to said control circuit; and
      an antenna electrically connected to said transmitting module for transmitting the eye image to said image-processing apparatus.

8. The eye activity monitoring system of claim 7, wherein said antenna operates with a frequency of between 2.4 and 2.5 GHz.

9. The eye activity monitoring system of claim 7, wherein said eye image is modulated by a Gaussian frequency shift keying and then transmitted to said image-processing means.

10. The eye activity monitoring system of claim 7, wherein the eye image is transmitted to the image-processing means by according to a Bluetooth wireless transmission protocol.

11. The eye activity monitoring system of claim 7, wherein the eye image is transmitted to said image-processing means according to an IEEE 802.11 wireless transmission protocol.

12. The eye activity monitoring system of claim 7, wherein said monitoring means further comprises at least one power supply positioned on said eye mask.

13. The eye activity monitoring system of claim 7, wherein said monitoring means further comprises a light emitting diode positioned on said eye mask for illumination.

14. The eye activity monitoring system of claim 7, wherein said image-sensing unit is a CCD or a CMOS image sensor.

15. The eye activity monitoring system of claim 7, wherein said image-sensing unit is a sensor without an IR filter and focus lens.

16. The eye activity monitoring system of claim 7, wherein the antenna is a planar antenna.

17. The eye activity monitoring system of claim 7, wherein the image-processing means comprises:
   a receiving means for receiving the eye image from said monitoring apparatus; and
   an image-processing means for generating an alarm signal based on the eye image.

18. The eye activity monitoring system of claim 17, wherein said image-processing means comprises:
   an image enhancing means for enhancing the eye image;
   a feature extracting means for acquiring features of the eye image;
   a judging means for judging a status of the eye of the user based on the feature of the eye image; and
   a means for generating the alarm signal when an abnormal event occurs according to the status of the eye output from the judging means.

* * * * *